(12) United States Patent
Phan et al.

(10) Patent No.: US 7,585,310 B2
(45) Date of Patent: Sep. 8, 2009

(54) MINIMALLY INVASIVE CLAMP

(75) Inventors: Huy D. Phan, San Jose, CA (US); Steven Ha, Hayward, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 354 days.

(21) Appl. No.: 11/035,944

(22) Filed: Jan. 14, 2005

(65) Prior Publication Data
US 2006/0161201 A1    Jul. 20, 2006

(51) Int. Cl.
*A61B 17/28* (2006.01)
(52) U.S. Cl. .................................... 606/207
(58) Field of Classification Search ......... 606/205, 606/207, 208; D24/143; 81/420, 424.5, 81/426, 426.5
See application file for complete search history.

(56) References Cited

U.S. PATENT DOCUMENTS

| | | | |
|---|---|---|---|
| 3,083,711 A * | 4/1963 | Ramsay | 606/201 |
| 3,369,550 A * | 2/1968 | Armao | 606/23 |
| 3,503,398 A | 3/1970 | Fogarty et al. | |
| 5,201,752 A * | 4/1993 | Brown et al. | 606/190 |
| 5,443,480 A | 8/1995 | Jacobs et al. | |
| 5,458,598 A * | 10/1995 | Feinberg et al. | 606/52 |
| 5,536,251 A * | 7/1996 | Evard et al. | 604/93.01 |
| 6,142,994 A | 11/2000 | Swanson et al. | |
| 6,273,887 B1 | 8/2001 | Yamauchi et al. | |
| 6,464,700 B1 | 10/2002 | Koblish et al. | |
| 6,517,536 B2 | 2/2003 | Hooven et al. | |
| 2002/0115993 A1 | 8/2002 | Hooven | |
| 2002/0138086 A1 | 9/2002 | Sixto et al. | |
| 2002/0183770 A1 * | 12/2002 | Anderson | 606/157 |
| 2003/0093068 A1 | 5/2003 | Hooven | |
| 2003/0158547 A1 | 8/2003 | Phan | |

OTHER PUBLICATIONS

PCT International Search Report dated Mar. 30, 2006 for Int. App. No. PCT/US2005/045147.

* cited by examiner

*Primary Examiner*—Anhtuan T Nguyen
*Assistant Examiner*—Ryan J Severson
(74) *Attorney, Agent, or Firm*—Vista IP Law Group LLP

(57) ABSTRACT

A clamp including first and second clamp members, at least one of which can be pivoted between an open orientation and a closed orientation.

43 Claims, 6 Drawing Sheets

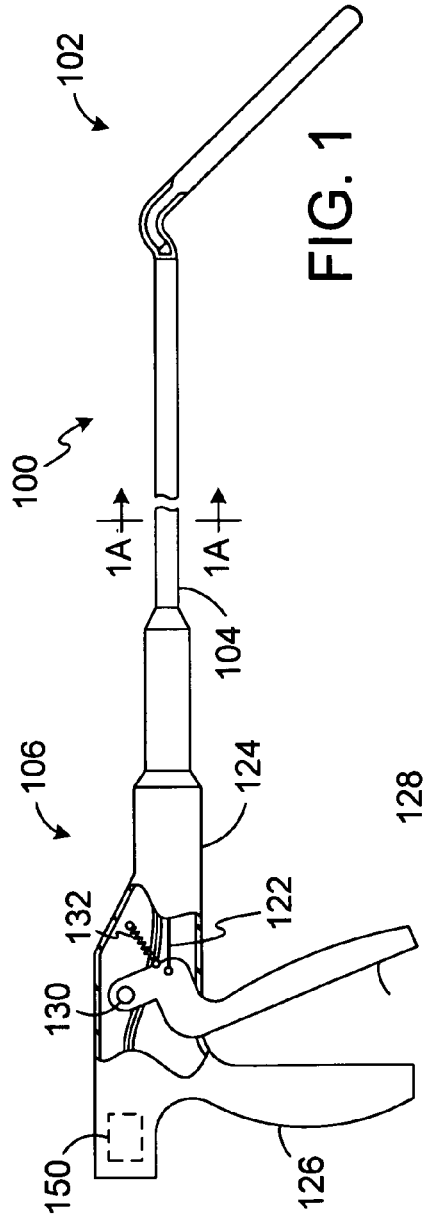
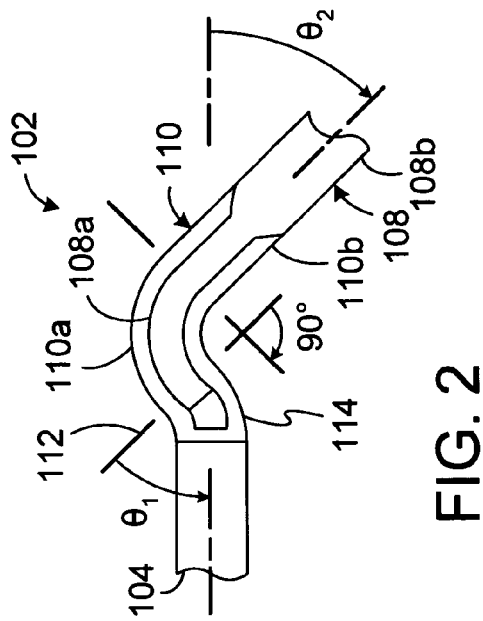
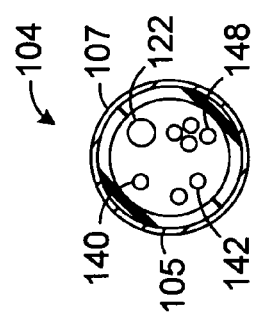

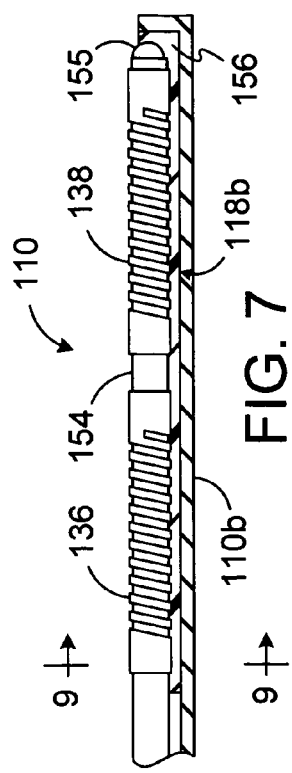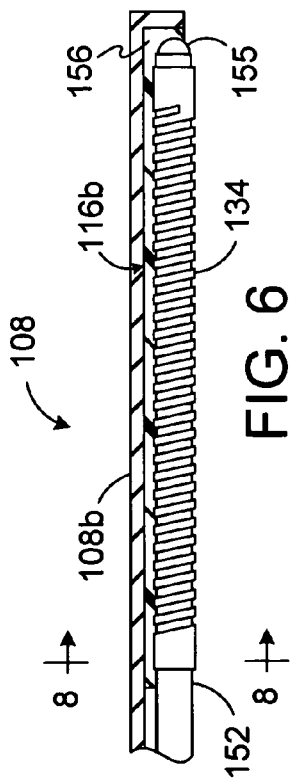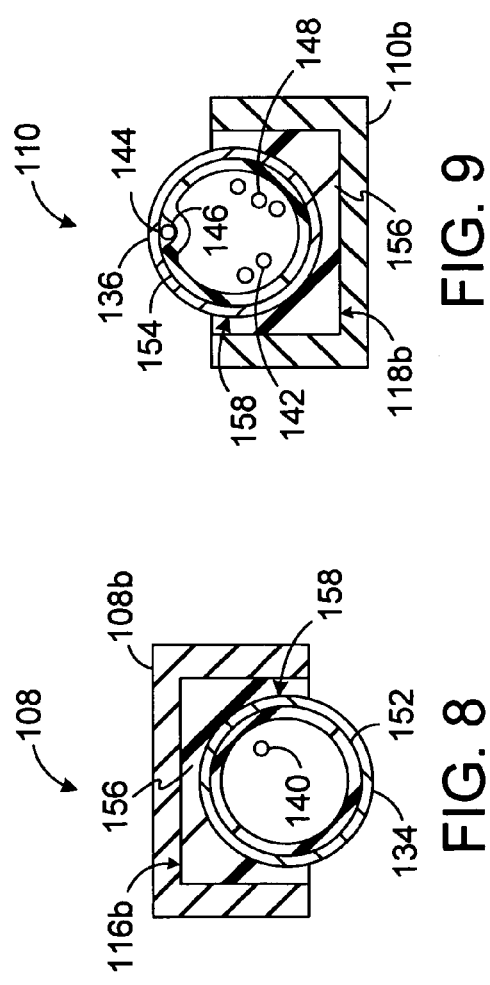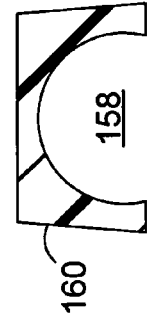

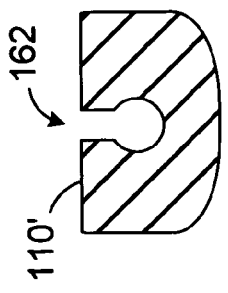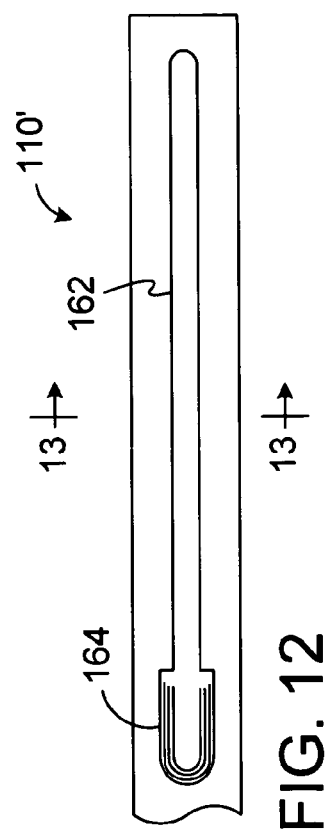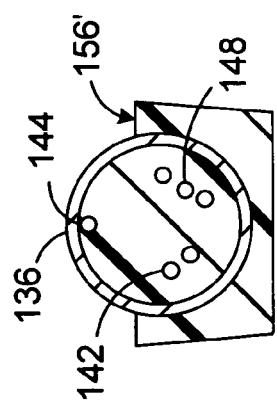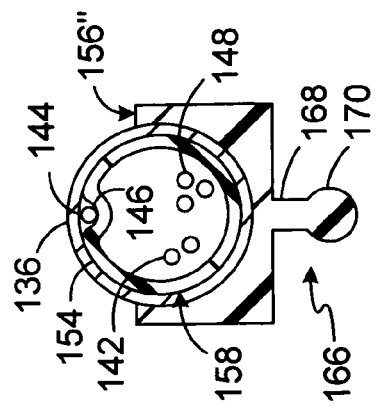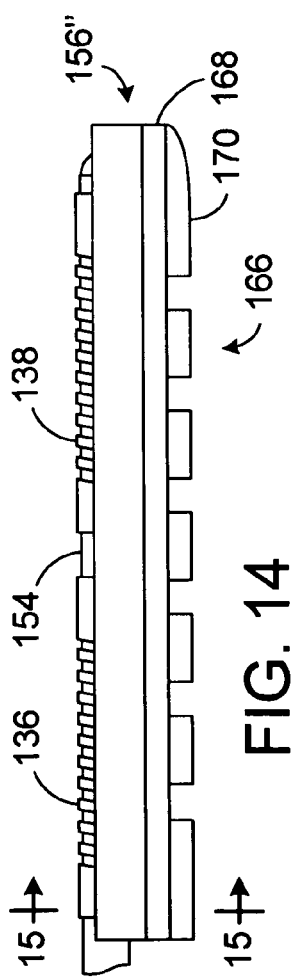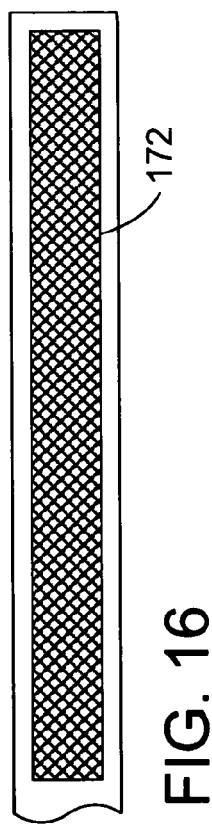

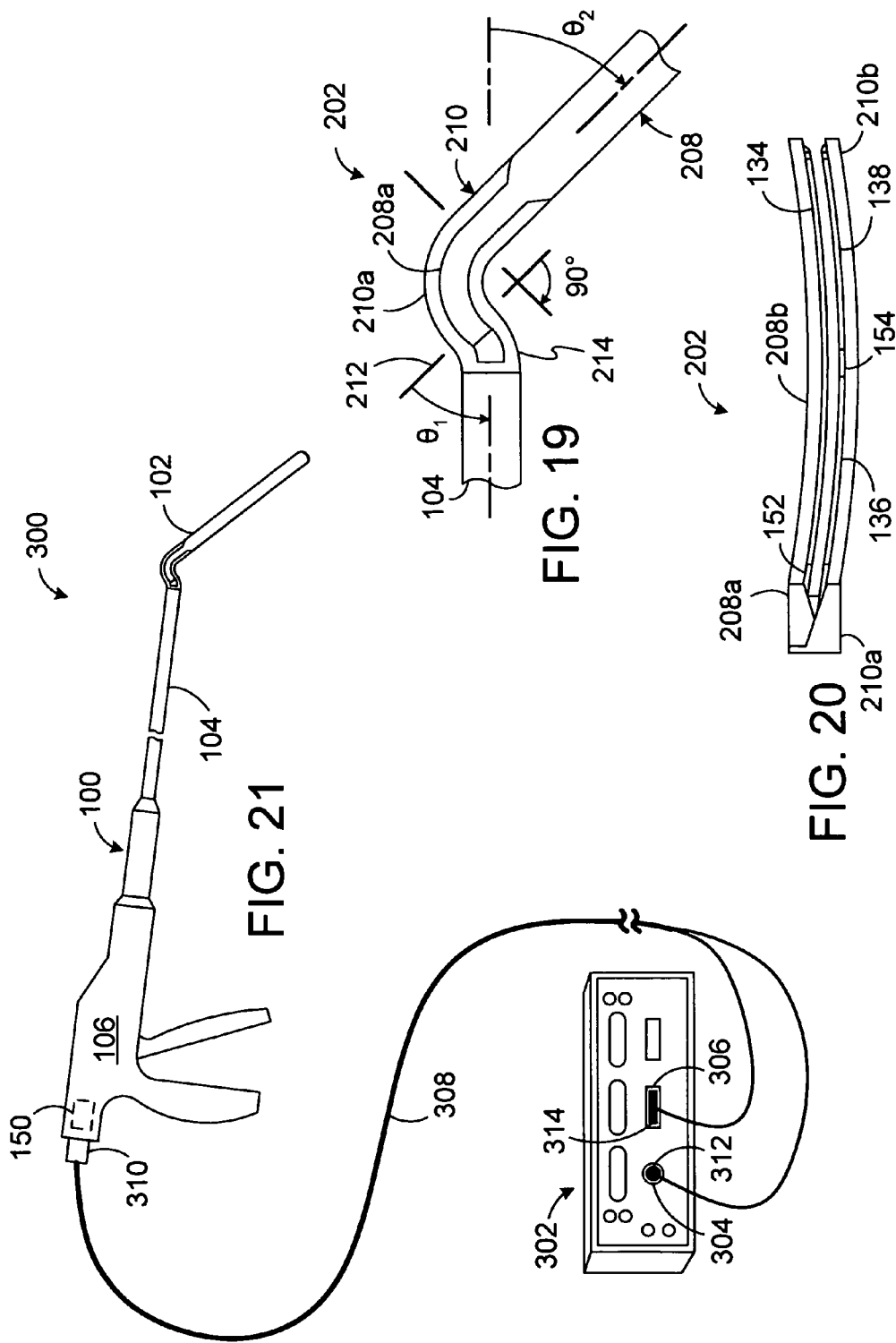

MINIMALLY INVASIVE CLAMP

BACKGROUND OF THE INVENTIONS

1. Field of Inventions

The present inventions relate generally to devices for performing operations on body tissue.

2. Description of the Related Art

Clamps are used in a wide variety of medical procedures. For example, clamps that carry electrodes or other energy transmission elements on opposable clamp members are used in a number of electrophysiology procedures, especially those in which the physician intends to position electrodes on opposite sides of a body structure to form a therapeutic lesion. Therapeutic lesions are frequently formed to treat conditions in the heart, prostate, liver, brain, gall bladder, uterus, breasts, lungs and other solid organs. Electromagnetic radio frequency ("RF") may, for example, be used to heat and eventually kill (i.e. "ablate") tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. The tissue coagulation energy is typically supplied and controlled by an electrosurgical unit ("ESU") during the therapeutic procedure. More specifically, after an electrophysiology device has been connected to the ESU, and the electrodes or other energy transmission elements on the device have been positioned adjacent to the target tissue, energy from the ESU is transmitted through the energy transmission elements to the tissue to from a lesion. The amount of power required to coagulate tissue ranges from 5 to 150 W.

Examples of clamp based devices which carry energy transmission elements are disclosed in U.S. Pat. No. 6,142,994, and U.S. Patent Pub. No. 2003/0158547 A1, which are incorporated herein by reference. In a typical clamp based procedure, a clamp will be used by the physician to position energy transmission elements on opposite sides of a tissue structure. Energy may then be transmitted through the tissue from one energy transmission element to the other, which is commonly referred to as bipolar energy transmission, or from each of the energy transmission elements to an indifferent electrode positioned at a remote location such as the patient's skin, which is commonly referred to as unipolar energy transmission.

Some clamps are designed such that the clamp members remain parallel to one another (or at least approximately parallel to one another) as the clamp moves from a closed orientation to an open orientation and back. Maintaining the parallel relationship serves a number of important purposes. For example, it may be important that the electrodes on the clamp members be parallel to one another when the tissue structure is engaged, regardless of the thickness of the tissue structure. The parallel relationship also reduces the maximum distance that the distal most portions of the clamp members will be from one another when the clamp is being positioned around a tissue structure, as compared to clamps with clamp members that are not configured to maintain a parallel relationship. One conventional method of insuring that the clamp members maintain a parallel relationship is to orient the clamp members such that they are both parallel to the axis about which they are pivoting. In those instances where the clamp includes a pair of arms that are pivotably connected to one another by a pivot pin, the parallel relationship has been heretofore accomplished by orienting the clamp members at 90 degrees to the arms at a location that is significantly distal of the pivot pin. Such clamps have an overall "L" shape.

The present inventors have determined that conventional clamps which maintain the clamp members in a parallel relationship are susceptible to improvement. For example, the present inventors have determined that it is very difficult to insert an L-shaped device through a small port (such as a trocar) during minimally invasive surgical procedures. The present inventors have also determined that the configuration of conventional clamps which maintain the clamp members in a parallel relationship results in a profile, when open, that can be too large for minimally invasive procedures. The present inventors have further determined that the configuration of conventional clamps which maintain the clamp members in a parallel relationship can result in the rotational misalignment of the clamp members when the clamp members are positioned around a tissue structure, which can result in poor electrode-tissue contact in electrophysiological applications.

SUMMARY OF THE INVENTIONS

A clamp in accordance with one example of a present invention includes a first clamp member including an angled portion defining an approximately 90 degree angle and a tissue engagement portion, a second clamp member including an angled portion defining an approximately 90 degree angle and a tissue engagement portion, and a redirection portion proximal to the first and second clamp member angled portions. Such a clamp provides a number of advantages. For example, although the tissue engagement portions will remain at least approximately parallel to one another, the clamp does not have an overall "L" shape and, therefore, is easier to advance into a patient though a port.

A clamp in accordance with one example of a present invention includes a first clamp member having a curved portion and a tissue engagement portion and a second clamp member having a curved portion and a tissue engagement portion extending from the curved portion. The first clamp member is pivotable relative to the second clamp member about a pivot axis located substantially at the proximal ends of the first and second clamp member curved portions. Such a clamp provides a number of advantages. For example, the present clamp has a smaller open orientation profile than an otherwise identical clamp where the curved portions begin at a location distally spaced from the pivot axis.

A clamp in accordance with one example of a present invention includes first and second clamp members having respective tissue engagement surfaces. The first clamp member is pivotable relative to the second clamp member about a pivot axis that is offset from the second clamp member tissue engagement surface by a predetermined non-zero distance. The first and second clamp members are configured such that the first and second clamp members will be rotationally aligned when the first clamp member tissue engagement surface and second clamp member tissue engagement surface are separated by the predetermined non-zero distance. Such a clamp provides a number of advantages. For example, the predetermined non-zero distance may be a distance corresponding to the thickness of the tissue structure (or structures) that the clamp is intended to engage, thereby assuring that the clamp members will be rotationally aligned when the tissue structure is engaged.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan, partial cutaway view of a clamp in accordance with one embodiment of a present invention.

FIG. 1A is a section view taken along line 1A-1A in FIG. 1.

FIG. 2 is an enlarged view of a portion of the clamp illustrated in FIG. 1.

FIG. 6 is a section view taken along line 6-6 in FIG. 3.

FIG. 7 is a section view taken along line 7-7 in FIG. 4.

FIG. 8 is a section view taken along line 8-8 in FIG. 6.

FIG. 9 is a section view taken along line 9-9 in FIG. 7.

FIG. 10 is a section view of the mounting device illustrated in FIGS. 6-8.

FIG. 11 is a section view of a mounting device and electrode arrangement in accordance with one embodiment of a present invention.

FIG. 12 is a plan view of a portion of a clamp member in accordance with one embodiment of a present invention.

FIG. 13 is a section view taken along line 13-13 in FIG. 12.

FIG. 14 is a side view of a mounting device and electrode arrangement in accordance with one embodiment of a present invention.

FIG. 15 is a section view taken along line 15-15 in FIG. 14.

FIG. 16 is a plan view of a portion of a clamp member in accordance with one embodiment of a present invention.

FIG. 19 is an enlarged view of a portion of a clamp in accordance with one embodiment of a presented invention.

FIG. 20 is an end view of the clamp illustrated in FIG. 19.

FIG. 21 is a perspective view of an electrophysiology system in accordance with one embodiment of a present invention.

DETAILED DESCRIPTION OF THE PREFERRED EMBODIMENTS

Figure 5:
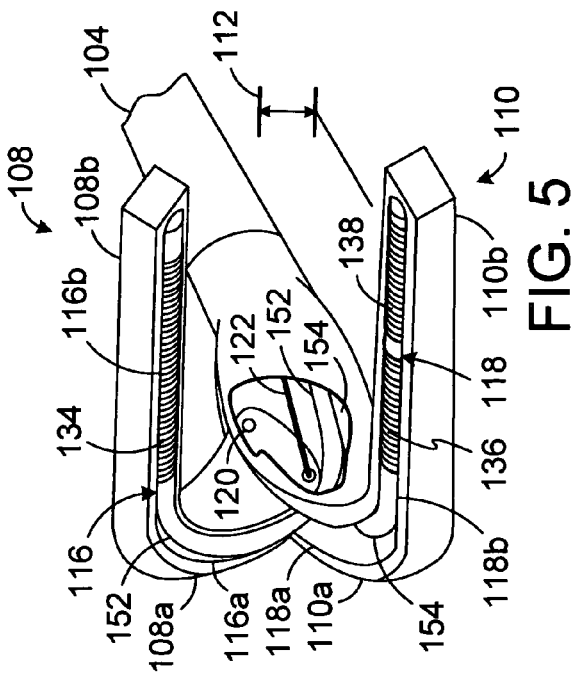
FIG. 5 is a perspective, partial cutaway view of a portion of the clamp illustrated in FIG. 1 with the clamp members in the open orientation.
Figure 4:
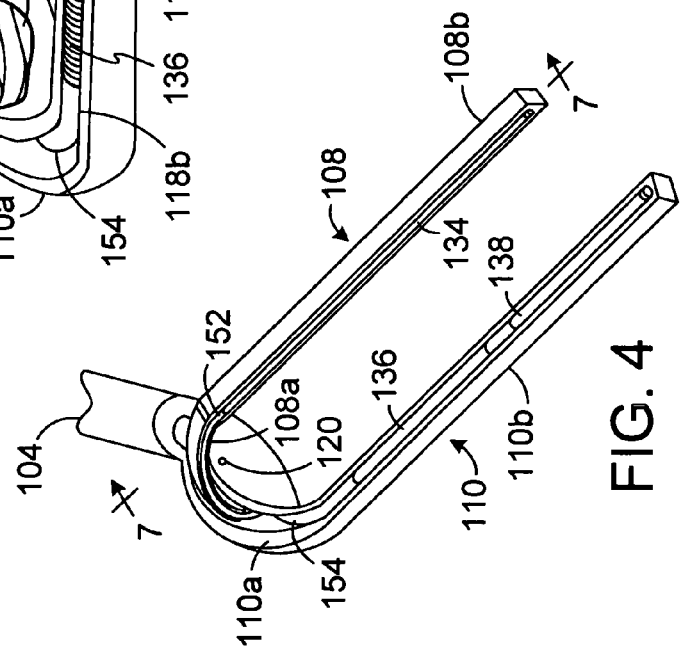
FIG. 4 is a perspective view of a portion of the clamp illustrated in FIG. 1 with the clamp members in the open orientation.
Figure 3:
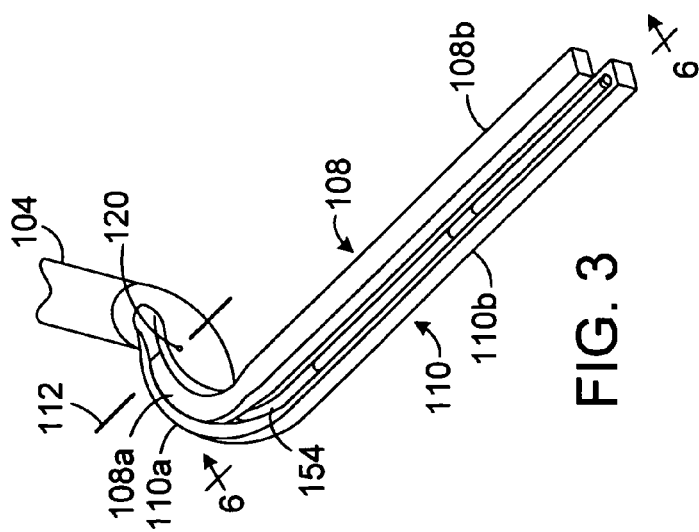
FIG. 3 is a perspective view of a portion of the clamp illustrated in FIG. 1 with the clamp members in the closed orientation.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
I. Introduction
II. Exemplary Clamp
III. Exemplary Electrophysiology System The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus, breasts, lungs, and other solid organs. The present structures may also be used in both electrophysiological and non-electrophysiological applications as well as both minimally invasive procedures and more invasive procedures such as open heart surgery.

II. Exemplary Clamp

One example of a clamp 100 in accordance with a preferred embodiment of a present invention is illustrated in FIGS. 1-10. The exemplary clamp 100 includes a tissue engagement device 102 that is carried on the distal end of a shaft 104 as well as a handle 106 that is carried on the proximal end of the shaft and used to move the tissue engagement device between the open and closed orientations illustrated in FIGS. 3-5.

The tissue engagement device 102 includes a first clamp member 108 and a second clamp member 110 and at least one of the first and second clamp members is movable relative to the other. In the exemplary implementation, the first clamp member 108 pivots relative to the second clamp member 110 about a pivot axis 112. The position of the second clamp member 110 is fixed relative to the shaft 104. Referring to FIG. 2, the first clamp member 108 includes an angled portion 108a and a tissue engagement portion 108b, and the second clamp member 110 includes an angled portion 110a and a tissue engagement portion 110b. The angled portions 108a and 110a create a 90 degree bend in the clamp members 108 and 110 that begins at the pivot axis 112, and the tissue engagement portions 108b and 110b extend linearly, in parallel, and in the same direction from the distal end of the angled portions. As a result, the clamp member tissue engagement portions 108b and 110b will remain parallel to one another as the tissue engagement device 102 moves between the open and closed orientations. The clamp member angled portions 108a and 110a may be curved, as shown, may define a sharp corner, or may be any other shape that results in a 90 degree bend.

It should be noted that although an exact 90 degree bend in the angled portions 108a and 110a is preferred, the bend may vary to some degree if applications so require. For example, angles within ±20 degree range of 90 degrees (i.e. angles that range from 70 degrees to 110 degrees) are acceptable is some circumstances and this range of angles is referred to herein as "approximately 90 degrees." Such variation will, of course, result in tissue engagement portions 108b and 110b that do not remain exactly parallel to one another as the tissue engagement device 102 moves between the open and closed orientations. The parallel to slightly non-parallel range associated with the 70-110 degree range of angles is referred to herein a "approximately parallel" and the equal to slightly not equal spacing along the length of the tissue engagement portions 108b and 110b is referred to herein as "approximately equal."

The exemplary clamp 100 also includes a redirection portion 114 that defines an angle $\theta_1$ in the opposite direction as the clamp member angled portions 108a and 110a. Referring more specifically to FIG. 2, the redirection portion 114 bends in the counter clockwise direction, while the clamp member angled portions 108a and 110a bend 90 degrees in the clockwise direction. As a result, the clamp member tissue engagement portions 108b and 110b are oriented at an angle $\theta_2$ relative to the distal end of the shaft 104. In the exemplary embodiment, angle $\theta_1$ is 45 degrees and, as a result, the clamp member tissue engagement portions 108b and 110b are oriented at an angle of 45 degrees relative to the distal end of the shaft 104. Angle $\theta_1$ may, however, be any suitable angle in the opposite direction of the bend in clamp member angled portions 108a and 110a.

There are a number of advantages associated with the configuration described above. For example, the two-angle configuration (i.e. the 90 degree angle and $\theta_1$) associated with the angled portions 108a and 108b and the redirection portion 114 allows the clamp 100 to perform the function associated with a 90 degree bend, i.e. clamp member tissue engagement portions 108b and 110b remain parallel to one another, in a clamp that does not have an overall "L" shape that is difficult to advance into a patient though a port. Instead of the clamp member tissue engagement portions 108a and 108b define an angle $\theta_2$ with the shaft that is less than 90 degrees, i.e. 45 degrees in the illustrated embodiment, which makes it much easier to maneuver the clamp into the patient.

Other advantages are associated with the location of the 90 degree bend relative to the pivot axis 112. The 90 degree bend in angled portions 108a and 110a preferably begins substantially adjacent to the pivot axis 112 (e.g. no more that about 10 mm to 20 mm distally from the pivot axis) and, in the illustrated embodiment, begins at the pivot axis. Such an arrangement results in a smaller open orientation profile for the tissue engagement device 102, as compared to an otherwise identical tissue engagement device where the 90 degree bend in the angled portions begins at a location distally spaced from the pivot axis. As used herein, the term "open orientation profile" refers to the space (or volume) occupied by tissue engagement devices when open.

Figure 17C:
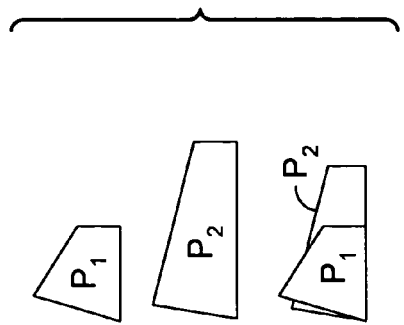
FIG. 17C is a diagrammatic representation of the open orientation profiles of the clamps illustrated in FIGS. 17A and 17B.
Figure 17B:
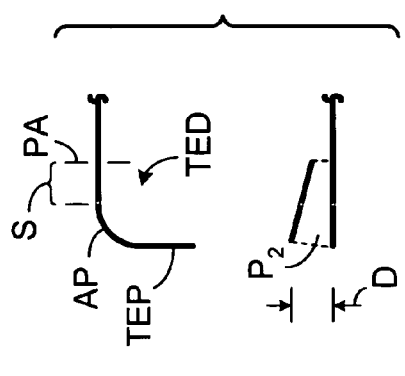
FIG. 17B is diagrammatic representation of a modified version of the clamp illustrated in FIG. 17A.
Figure 17A:
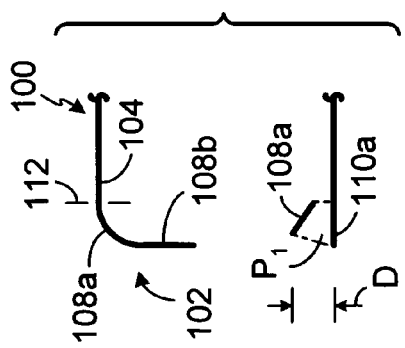
FIG. 17A is diagrammatic representation of a clamp in accordance with one embodiment of a present invention.

This aspect of the exemplary embodiment is diagrammatically illustrated in FIGS. 17A-17C. Referring first to FIG. 17A, the exemplary clamp 100 is diagrammatically shown from the top and side and is open a distance D. The beginning (or proximal end) of the 90 degree bend in the clamp member angled portions is located at the pivot axis 112. The tissue engagement device 102 defines a profile $P_1$. An otherwise identical clamp, with clamp member angled portions AP and tissue engagement portions TEP is diagrammatically shown in FIG. 17B from the top and side and is open the same distance D. Here, however, the beginning (or proximal end) of the 90 degree bend in the angled portions AP is distally spaced a distance S from the pivot axis PA. The tissue engagement device TED defines a profile $P_2$. Profiles $P_1$ and $P_2$ are shown individually and superimposed over one another in FIG. 17C. The profile $P_1$ of the present tissue engagement device 102 is clearly smaller than the profile $P_2$ of the tissue engagement device with the pivot axis PA proximally spaced from the beginning of the bend in the clamp member angled portions AP. Accordingly, the present clamp 100 requires far less space within the patient to open the tissue engagement device 102. This is especially important in instances where there is limited space to open and close clamp members, such as during procedures within the pericardial space.

The redirection portion 114 illustrated in FIG. 2 may be part of the tissue engagement device 102, the shaft 104, or a separate structural element that is located between the tissue engagement device and the shaft. In the illustrated embodiment, the redirection portion 114 is part of the tissue engagement device 102 and is integral with the second clamp member curved portion 110a. With respect to the line of demarcation between the two in the illustrated embodiment, the redirection portion 114 ends, and the second clamp member curved portion 110a begins, at the pivot axis 112.

Referring to FIG. 5, the first clamp member 108 in the exemplary embodiment includes a slot 116 with an angled portion 116a and a linear portion 116b, while the second clamp member 110 includes a slot 118 with an angled portion 118a and a linear portion 118b. The angled portions of the slots are coextensive with the angled portions of the clamp members and the linear portions of the slots are coextensive with the tissue engagement portions. The first clamp member 108 is connected to the second clamp member 110 by a pivot pin 120 that is coaxial with the pivot axis 112. The pivot pin 120 secures the first clamp member angled portion 108a within the slot angled portion 118a in the second clamp member 110, thereby allowing the first clamp member 108 to pivot between the closed orientation illustrated in FIG. 3 and the open orientation illustrated in FIGS. 4 and 5.

With respect to actuation of the engagement device 102, and as illustrated for example in FIG. 5, the exemplary clamp 100 includes a control element 122 (such as a stranded wire or a rod) that is secured to the first clamp member angled portion 108a in spaced relation to the pivot pin 120. Distal movement of the control element 122 pushes the clamp member 108 about the pivot pin 120 from the closed orientation illustrated in FIG. 3 to the open orientation illustrated in FIGS. 4 and 5. It should be noted that the clamp may, alternatively, be configured such that proximal movement of the control element 122 causes the engagement device 102 to open.

Turning to FIG. 1, the proximal end of the control element 122 is associated with, and the control element is actuated by, the handle 106. Although the present inventions are not limited to any particular type of handle, the exemplary handle 106 includes a handle body 124 with a grip portion 126 and a trigger 128 that pivotably connected to the handle body by a pin 130. Injection molded plastics such as PVC or glass-filled polycarbonate may be used to form the handle body 124 and trigger 128. The trigger 128 is biased to the orientation illustrated in FIG. 1, which results in the tissue engagement device 102 being in the open orientation illustrated in FIGS. 4 and 5, by a spring (or other biasing device) 132. The tissue engagement device 102 is closed when the trigger 128 is moved toward the grip portion 126, thereby pulling the control element 122 in the proximal direction.

The clamp members 108 and 110 may be formed from any suitable material. By way of example, but not limitation, the clamp members may be formed from injection molded plastic or injection molded metals such as boron/brass. The clamp members 108 and 110 may also be machined or stamped out of stainless steel. The dimensions of the clamp members 108 and 110 will vary from application to application. In those instances where the clamp 100 is intended for use in cardiovascular applications, the tissue engagement portions 108b and 110b will typically be located about 1 cm to 10 cm from the pivot axis 112 (measured in a direction perpendicular to the pivot axis) and will be about 1 cm to 10 cm in length (measured from the distal ends of the angled portions 108a and 110a). When in the closed orientation, the clamp members will be about 2 mm to 12 mm apart, depending on the intended application and will be about 4 mm to 5 mm apart in the illustrated embodiment.

The shaft 104 is preferably tubular and may be rigid, malleable or flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. Clamps including a flexible shaft (or a shaft in which at least the distal portion is flexible) may also include steering functionality in order to assist the physician with the positioning of the tissue engagement device 102. The shaft 104 in the illustrated embodiment is malleable and consists of a malleable hypotube 105 with an outer polymer jacket 107, as illustrated in FIG. 1A. Stainless steel is a suitable material for the malleable hypotube 105. The diameter of the shaft 104 will typically be about 3 mm to 10 mm. The length will depend on the intended application, and may be from 20 cm to 40 cm for cardiovascular applications.

The exemplary clamp 100 is adapted for use in electrophysiological procedures and, to that end, includes electrodes or other energy transmission elements that may be used to perform diagnostic or therapeutic operations on tissue. Although such electrophysiology clamps may be operated in bipolar and unipolar modes, the exemplary clamp 100 is configured so as to be especially useful in a bipolar mode wherein energy is transmitted through tissue from one or more energy transmission elements associated with the first clamp member 108 to one or more energy transmission elements associated with the second clamp member 110. To that end, and as illustrated for example in FIGS. 3-9, the first clamp member 108 carries an electrode 134 and the second clamp member 110 carries a pair of electrodes 136 and 138 that may be independently controlled. Typically, energy will be transmitted by the electrodes 136 and 138 and returned to the energy source by way of the electrode 134. This arrangement provides for higher fidelity control of the overall region that is transmitting energy and a gap free, constant potential region on the return side.

The electrodes 134, 136 and 138 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068.

Alternatively, the electrodes 134, 136 and 138 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Still other types of electrodes are formed from electroless plated copper on a polyimide film or tubular substrate. Gold, nickel or silver should be plated over the copper for electrochemical stability and improved biocompatibility. The plating can be applied in continuous form (up to about 1-2 cm in length at most) or can be applied in a pattern that is designed to improve current density distributions and/or electrode flexing characteristics. Temperature sensors (e.g. thermocouples) may be incorporated into the electrode structure by placing the temperature sensors in a channel in the polyimide film or an underlying tubular substrate and then plating over them.

The electrodes 136 and 138 in the exemplary embodiment are preferably about 1.5 cm to 4 cm in length with about 1 mm to 3 mm spacing, which will result in the creation of continuous lesion patterns in tissue when coagulation energy is applied simultaneously to the electrodes. The length of the electrode 134 is preferably the combined length of the electrodes 136 and 138, including the spacing therebetween, so that the overall electrode length on the first and second clamp members 108 and 110 is the same. The electrode 134 will be about 0 mm to 10 mm from the electrodes 136 and 138 in the illustrated embodiment when the tissue engagement device 102 is in the closed orientation.

The electrode 134 is connected to a power wire 140, while the electrodes 136 and 138 are connected to power wires 142, as shown in FIGS. 8 and 9. A plurality of temperature sensors 144 (FIG. 9), such as thermocouples or thermistors, may be located on, under, abutting the longitudinal end edges of, or in between, the electrodes 136 and 138. A reference thermocouple (not shown) may also be provided. In the exemplary implementation, temperature sensors 144 are located at both longitudinal ends of each of the electrodes 136 and 138. The temperature sensors 144 are also located within a linear channel 146 that is formed in the tubular member 154 (discussed below). The linear channel 146 insures that the temperature sensors will all face in the same direction (e.g. facing tissue) and be arranged in linear fashion. Signal wires 148 are connected to each of the temperature sensors 144.

The power wires 140 and 142 extend through the clamp member 102 and shaft 104, and into the handle 106 where they are connected to a connector 150, such as a PC board, within the handle 106 (FIGS. 1 and 1A). The signal wires 148 also extend through the clamp member 102 and shaft 104, and into the handle 106 where they are connected to the connector 150. The power wires 142 and signal wires 148 will typically be twisted into respective groups.

In accordance with another aspect of the exemplary implementation, the pivot axis 112 is positioned such that the clamp member tissue engagement portions 108b and 110b will be aligned with one another when the tissue engagement device 102 is open a predetermined distance (i.e. there is a predetermined distance between the electrode 134 and the electrodes 136 and 138). Typically, this distance will correspond to the expected thickness of the tissue structure that the clamp 100 is intended to grip, or the average thickness of such tissue structures. For example, if the expected thickness of the tissue structure is 10 mm, then the predetermined distance may be about 10 mm. Conversely, if the expected thickness of the tissue structures ranges from 1 to 10 mm, then the predetermined distance may be about 5 mm.

As illustrated for example in FIG. 5, the pivot axis 112 is vertically offset from the top of the clamp member tissue engagement portion 110b, which is the top of the electrodes 136 and 138 in the exemplary embodiment. For example, the offset is about 10 mm in those instances where the expected thickness of the tissue structures is 10 mm, and is about 5 mm in those instances where the expected thickness of the tissue structures ranges from 1 to 10 mm. Such an arrangement insures that the tissue engagement portions 110a and 110b will be properly oriented when the tissue engagement device 102 engages tissue, which results in good electrode tissue contact.

Figure 18B:
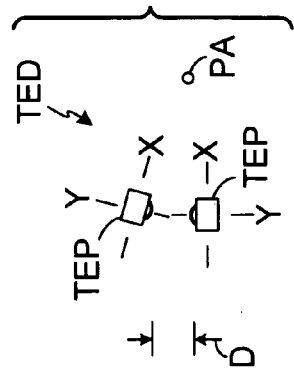
FIG. 18B is diagrammatic representation of a modified version of the clamp illustrated in FIG. 18A.
Figure 18A:
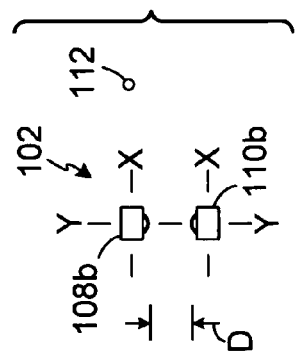
FIG. 18A is diagrammatic representation of a clamp in accordance with one embodiment of a present invention.

This aspect of the exemplary embodiment is diagrammatically illustrated in FIGS. 18A and 18B. Referring first to FIG. 18A, the tissue engagement device 102 of the exemplary clamp 100 is diagrammatically shown open a distance D. Because the pivot axis 112 is offset in the Y-direction by the distance D from the tissue engagement portion 110b (also note FIG. 5), the Y-axes of the tissue engagement portions 108b and 110b are aligned with one another and the X-axes are parallel to one another. The X and Y-axes are the horizontal and vertical axes that pass through the center of the tissue engagement portions when viewed from the end in the manner shown in FIG. 18A. The electrodes are also diametrically aligned. In other words, the tissue engagement portion 108b is rotationally aligned with the tissue engagement portion 110b when the clamp is open the distance D.

An otherwise identical clamp, including a tissue engagement device TED with clamp members having tissue engagement portions TEP, is diagrammatically shown in FIG. 18B open the same distance D. Here, however, the pivot axis PA is located much closer to the top of the lower clamp member tissue engagement portion TEP. As a result, the tissue engagement portions TEP are not aligned when the tissue engagement device TED is open the distance D. The Y-axes of the tissue engagement portions 110a and 110b are misaligned with one another and the X-axes are not parallel to one another because the tissue engagement portion 108b is rotationally offset from the tissue engagement portion 110b. Such rotational misalignment can, for example, result in poor electrode-tissue contact, as well as lower conductive surface area, in electrophysiology clamps because the corner of the top tissue engagement portion will engage tissue and push it away from the electrode.

It should also be noted that, with respect to instances where a clamp is open a distance D1 (not shown), which is greater than distance D, the clamp illustrated in FIG. 18A will exhibit much less rotational sensitivity than the clamp illustrated in FIG. 18B. The rotational offset of the clamp illustrated in FIG. 18A will be lower than that illustrated in FIG. 18B because the clamp illustrated in FIG. 18A is only rotationally offset as it travels from distance D (where there is no offset) to distance D1, while the clamp illustrated in FIG. 18B becomes increasingly more rotationally offset over its entire range of motion. The clamp illustrated in FIG. 18A has a "head start" equal to the offset of the pivot axis 112 (here, distance D).

There are a variety of ways to mount electrodes or other energy transmission elements on the clamp members 108 and 110, either permanently or temporarily, and the electrophysiological implementations of the present inventions are not limited to any particular mounting arrangement. In the illustrated embodiment, the electrode 134 is carried on a tubular member 152 and the electrodes 136 and 138 are carried on a tubular member 154, as shown in FIGS. 3-9. The distal portions of the tubular members 152 and 154 are carried by mounting devices 156, which are identical in the illustrated embodiment. The proximal portions of the tubular members 152 and 154 extend though the tissue engagement device 102 into the shaft 104, which may in some implementations be sealed with silicon rubber or low durometer urethane or polyurethane. The distal ends of the tubular members may be closed with tip members 155.

The mounting devices 156, which extend from the distal ends of the clamp member tissue engagement portions 110a and 110b to about the clamp member angled portions 108a and 108b, include a groove 158 that is configured to receive the tubular member 152 and electrode 134 (or tubular member 154 and electrodes 136 and 138). The mounting devices 156 may be shaped and sized such that they can be press fit into the slot linear portions 116b and 118b. As illustrated in FIG. 10, for example, the mounting devices 156 may have an overall trapezoidal shape with slanted sides 160. Alternatively, or in addition, adhesive may be used to secure the mounting devices 156 within the clamp member slots 116 and 118. About 20% of the electrode surface (i.e. about 75° of the 360° circumference) is exposed in the illustrated embodiment and adhesive may be used to hold the tubular members and electrodes in place within the groove 158. The mounting devices 156 are also configured such that the electrode 134 will be parallel to the electrodes 136 and 138. Other structures for securing electrodes or other energy transmission devices to clamp members are discussed below with reference to FIGS. 11-15.

With respect to dimensions and materials, the tubular members 152 and 154 in the illustrated embodiment are flexible structures which have an outer diameter that is, depending on the diameter of the electrodes 134, 136 and 138, typically between about 1.5 mm and about 3 mm. The tubular members 152 and 154 in the illustrated embodiment, which are intended for use in cardiovascular applications, have an outer diameter of about 2 mm. Suitable tubular members materials include, for example, flexible biocompatible thermoplastic tubing such as unbraided Pebax® material, polyethylene, or polyurethane tubing. The mounting devices 156 are preferably formed from flexible, electrically non-conductive materials such as urethane.

The exemplary clamp 100 may also be provided with tissue cooling apparatus (not shown). For example, at least the exposed portions of the electrodes 134, 136 and 138 may be covered with porous, wettable structures that are configured to be saturated with and retain ionic fluid (such as saline) prior to use so that energy may be transmitted to and from the associated electrodes by way of the ionic fluid. Suitable materials include foams, such as open cell foams, reticulated foams, non-reticulated foams, fine cell foams and hydrocolloide foams. Other suitable materials include hydrogels, thick woven biocompatible materials (e.g. Dacron®), cotton and cellulose.

As noted above, there are a variety of ways to mount electrodes or other energy transmission devices on the tissue engagement device 102. For example, instead of mounting the electrodes or other energy transmission devices on the tissue engagement device 102 with the tubular member and mounting device arrangement described above, the tubular member may be eliminated and the electrodes may be carried by the mounting device itself. Here, the electrodes 134, 136 and 138 and temperature sensors 144 (if present), with power wires 140 and 142 and signal wires 148 (if present) attached, may be placed in a mold into which a suitable material, such as urethane or polyurethane, is injected. One example of a mounting device produced by such a process is represented by reference numeral 156' in FIG. 11 and can be mounted in a slotted clamp members in the manner described above with reference to FIGS. 6-10.

Another clamp in accordance with the present inventions includes the mounting arrangement illustrated in FIGS. 12 and 13. The clamp is otherwise identical to the clamp 100 illustrated in FIGS. 1-10 similar reference numerals are used to represent similar elements in order to eliminate the need for redundant discussion. The clamp is configured such that a pair of conventional soft, deformable inserts (not shown) may be removably carried by the clamp members and allow the clamp to firmly grip a bodily structure without damaging the structure. To that end, the clamp members (only clamp member 110' is shown) each include a slot 162 that is provided with a sloped inlet area 164 and the inserts include mating structures that are removably friction fit within the slots. This allows the clamp to be used in non-electrophysiological applications.

The inserts may also be removed and replaced with a device that mounts one or more electrodes on the clamp members for electrophysiological procedures. For example, as illustrated in FIGS. 14 and 15, a mounting device 156" may be used to mount one or more electrodes on the clamp member 110'. The mounting device 156" includes a connector 166 with a relatively thin portion 168 and a relatively wide portion 170, which may consist of a plurality of spaced members (as shown) or an elongate unitary structure, in order to correspond to the shape of the slot 162. The electrode(s) is carried by a tubular member, which are in turn positioned within a groove 158. The same arrangement may be used to mount one or more electrodes on the other clamp member if desired.

Turning to FIG. 16, clamps in accordance with the present inventions, and which are otherwise identical to the clamp 100 illustrated in FIG. 1, may be configured to simply grasp tissue. Such clamps may be provided with clamp members (only clamp member 110" is shown) with a textured gripping surface 172.

As illustrated for example in FIGS. 19 and 20, the tissue engagement portions of clamp members in accordance with the present inventions may also have a curvilinear shape so long as the distance between vertically aligned points is the same over the length of the curvilinear shape. The tissue engagement device 202 is essentially identical to the tissue engagement device 102 and similar elements are represented by similar reference numerals. For example, the tissue engagement device 202 includes clamp members 208 and 210 with angled portions 208a and 210a and tissue engagement portions 208b and 210b. The clamp member 208 pivots about an axis 212 and a redirection portion 214 is also provided. The clamp member 202 may also be used in conjunction with shaft 104 and handle 106 described above, or any other suitable clamp apparatus. Here, however, the tissue engagement portions 208b and 210b have a curvilinear shape. The tissue engagement portions 208b and 210b are also co-planar in that, when in the closed orientation illustrated in FIG. 20, they lie in a common plane that is parallel to the pivot axis 212.

III. Exemplary Electrophysiology System

As illustrated for example in FIG. 21, an exemplary surgical system 300 in accordance with one embodiment of a present invention includes the clamp 100 and an ESU 302. The ESU 302, supplies and controls power to the electrodes on the clamp 100. A suitable ESU is the Model 4810A ESU sold by Boston Scientific Corporation of Natick, Mass., which is capable of supplying and controlling RF power in both bipolar and unipolar modes on an electrode-by-electrode basis. Such electrode-by-electrode power control is sometimes referred to as "multi-channel control." Typically, power will be controlled as a function of the temperature at each electrode in order to insure that tissue is coagulated without over-heating and causing coagulum and charring. With respect to temperature sensing, temperature at the electrodes 136 and 138 is measured by the aforementioned temperatures sensors 144. Alternatively, in those instances where temperature sensors are not employed, the respective temperatures at the electrodes 136 and 138 may be determined by measuring impedance at each electrode.

The exemplary ESU 302 illustrated in FIG. 21 is provided with a power output connector 304 and a pair of return connectors 306. A cable 308 may be used to connect the clamp 100 to the power and return connectors 304 and 306. To that end, the cable 308 includes a connector 310 that is configured to be connected to the connector 150 in the handle 106 and power and return connectors 312 and 314 that are respectively configured to be connected to the power and return connectors 304 and 306. As such, the electrodes 136 and 138 and temperature sensors 144 may be connected to the ESU power output connector 304, and the electrode 134 may be connected to the return connector 306. The ESU power output and return connectors 304 and 306 may have different shapes to avoid confusion and the cable power and return connectors 312 and 314 may be correspondingly shaped. For example, the power connectors have a generally circular shape and the return connectors have a generally rectangular shape. Additional information concerning suitable temperature sensing and RF power supply and control is disclosed in U.S. Pat. Nos. 5,456,682, 5,582,609, 5,755,715 and U.S. Patent Pub. No. 2004/0059325 A1.

There are a variety of applications for such as system. One example is the formation of transmural epicardial lesions to isolate the sources of focal (or ectopic) atrial fibrillation and, more specifically, the creation of transmural lesions around the pulmonary veins. Access to the heart may be obtained via a thoracotomy, thoracostomy or median sternotomy. Ports may also be provided for cameras and other instruments. Lesions may be created around the pulmonary veins individually or, alternatively, lesions may be created around pairs of pulmonary veins. For example, a first transmural epicardial lesion may be created around the right pulmonary vein pair and a second transmural epicardial lesion may be created around the left pulmonary vein pair. This may be accomplished by inserting the clamp 100 into the patient through a port, opening the tissue engagement device 102, placing the tissue engagement portions 108b and 110b on opposite sides of a pulmonary vein pair, closing the tissue engagement device, and transmitting tissue coagulation energy from the electrodes 136 and 138 to the electrode 134. Thereafter, if needed, a linear transmural epicardial lesion may be created between the right and left pulmonary vein pairs. A linear transmural lesion that extends from the lesion between the right and left pulmonary vein pairs to the left atrial appendage may also be formed. Alternatively, a single lesion may be formed around all four of the pulmonary veins.

Although the inventions disclosed herein have been described in terms of the preferred embodiments above, numerous modifications and/or additions to the above-described preferred embodiments would be readily apparent to one skilled in the art. By way of example, but not limitation, the present inventions include electrophysiology systems that include a power supply and control device and a clamp defined any one of the claims set forth below. It is intended that the scope of the present inventions extend to all such modifications and/or additions and that the scope of the present inventions is limited solely by the claims set forth below.

We claim:

1. A clamp, comprising:
an elongate shaft extending along a first axis and including a distal end;
a redirect portion located at the distal end of the elongate shaft and having a distal end, the redirect portion bending in a first direction with respect to the first axis, wherein an angle $\theta_1$ is defined between the redirect portion bending in the first direction and the first axis;

a pivot axis defined through the redirect portion;

a first clamp member affixed to the distal end of the redirect portion, the first clamp member including an angled portion beginning at the pivot axis and extending in a second direction opposite of the first direction to define an angle $\theta_2$ relative to the first axis and an approximately 90 degree angle relative to the redirect portion bending in the first direction, the first clamp member including a tissue engagement portion extending from the angled portion and being substantially parallel to the second direction and the pivot axis; and a second clamp member being pivotable relative to the first clamp member via the pivot axis, the second clamp member including an angled portion beginning at the pivot axis and extending in the second direction to also define an angle $\theta_2$ relative to the first axis and an approximately 90 degree angle relative to the redirect portion bending in the first direction, the second clamp member including a tissue engagement portion extending from the angled portion and being substantially parallel to the second direction and the pivot axis.

2. A clamp as claimed in claim 1, wherein the angle $\theta_1$ is approximately 45 degrees.

3. A clamp as claimed in claim 1, further comprising:
at least one energy transmission element carried by at least one of the first and second clamp member tissue engagement portions.

4. A clamp as claimed in claim 1, wherein the angle $\theta_1$ is also defined between the pivot axis and the first axis of the shaft.

5. A clamp as claimed in claim 1, wherein the first and second clamp member tissue engagement portions are substantially linear.

6. A clamp as claimed in claim 1, wherein the first and second clamp member tissue engagement portions are parallel to one another and remain parallel to one another as the second clamp member pivots.

7. A clamp as claimed in claim 1, wherein the redirect portion is integral with the first clamp member angled portion.

8. A clamp as claimed in claim 1, further comprising:
a handle disposed at a proximal end of the shaft; and
an actuation device positioned within the shaft and associated with the handle of one of the first and second clamp members.

9. The clamp as claimed in claim 1, wherein the elongate shaft is substantially linear.

10. The clamp as claimed in claim 1, wherein a position of the first clamp member is fixed relative to the elongate shaft.

11. The clamp as claimed in claim 1, wherein the angle $\theta_2$ is approximately 45 degrees.

12. The clamp as claimed in claim 1, wherein the first and second clamp members are parallel to each other and aligned with each other when the first and second clamp members are opened by a predetermined distance.

13. The clamp as claimed in claim 1, wherein the redirect portion forms an outer surface of the clamp.

14. The clamp as claimed in claim 1, wherein the shaft forms an outer surface of the clamp.

15. The clamp as claimed in claim 1, wherein the angled portions of the respective first and second clamp members extend beyond a first side of the shaft, and the tissue engagement portions of the respective first and second members extend beyond a second, opposite side of the shaft when placed in both open and closed positions.

16. The clamp as recited in claim 1, wherein the pivot axis does not extend through the shaft.

17. A clamp, comprising:
an elongate shaft extending along a first axis and including a distal end;

a redirect portion located at the distal end of the elongate shaft and having a distal end, the redirect portion bending in a first direction with respect to the first axis, wherein an angle $\theta_1$ is defined between the redirect portion bending in the first direction and the first axis;

a pivot axis defined through the redirect portion;

a first clamp member originating from the distal end of the redirect portion, the first clamp member including an angled portion beginning at the pivot axis and extending in a second direction opposite of the first direction to define an angle $\theta_2$ relative to the first axis and an approximately 90 degree angle relative to the redirect portion bending in the first direction, the first clamp member including a tissue engagement portion having a contact surface and extending from the angled portion such that the contact surface of the first clamp member is substantially parallel to the second direction and the pivot axis; and a second clamp member being pivotable relative to the first clamp member via the pivot axis, the second clamp member including an angled portion beginning at the pivot axis and extending in the second direction to also define an angle $\theta_2$ relative to the first axis and an approximately 90 degree angle relative to the redirect portion bending in the first direction, the second clamp member including a tissue engagement portion having a contact surface and extending from the angled portion such that the contact surface of the second clamp member is substantially parallel to the second direction and the pivot axis.

18. A clamp as claimed in claim 17, wherein the angle $\theta_1$ is approximately 45 degrees.

19. A clamp as claimed in claim 17, wherein the first and second clamp member tissue engagement portions are substantially linear.

20. A clamp as claimed in claim 17, wherein the first and second clamp member tissue engagement portions are parallel to one another when the clamp is closed and remain at least approximately parallel to one another as the second clamp member pivots.

21. A clamp as claimed in claim 17, further comprising:
at least one energy transmission element carried by at least one of the first and second clamp member tissue engagement portions.

22. The clamp as claimed in claim 17, wherein the elongate shaft is substantially linear.

23. The clamp as claimed in claim 17, wherein a position of the first clamp member is fixed relative to the elongate shaft.

24. The clamp as claimed in claim 17, wherein the angle $\theta_2$ is approximately 45 degrees.

25. The clamp as claimed in claim 17, wherein the first and second clamp members are parallel to each other and aligned with each other when the first and second clamp members are opened by a predetermined distance.

26. The clamp as claimed in claim 17, wherein the redirect portion forms an outer surface of the clamp.

27. The clamp as claimed in claim 17, wherein the shaft forms an outer surface of the clamp.

28. The clamp as claimed in claim 17, wherein the angled portions of the respective first and second clamp members extend beyond a first side of the shaft, and the tissue engagement portions of the respective first and second members extend beyond a second, opposite side of the shaft when placed in both open and closed positions.

29. The clamp as recited in claim 17, wherein the pivot axis does not extend through the shaft.

30. A clamp, comprising:
an elongate shaft extending along a first axis and including a distal end;
a redirect portion located at the distal end of the elongate shaft and having a distal end, the redirect portion bending in a first direction, wherein an angle $\theta_1$ is defined between the redirect portion bending in the first direction and the first axis;
a pivot axis defined through the redirect portion;
a first clamp member originating from the distal end of the redirect portion, the first clamp member including an angled portion beginning at the pivot axis and extending in a second direction opposite of the first direction to define an angle $\theta_2$ relative to the first axis and an approximately 90 degree angle relative to the redirect portion bending in the first direction, the first clamp member including a tissue engagement portion extending from the angled portion and being substantially parallel to the second direction and the pivot axis; and
a second clamp member being pivotable relative to the first clamp member via the pivot axis, the second clamp member including an angled portion beginning at the pivot axis and extending in the second direction to also define an angle $\theta_2$ relative to the first axis and an approximately 90 degree angle relative to the redirect portion bending in the first direction, the second clamp member including a tissue engagement portion extending from the angled portion and being substantially parallel to the second direction and the pivot axis;
wherein the pivot axis is offset with respect to the second clamp member such that the tissue engagement portions of the first and second clamp members extending in the second direction remain aligned with each other when the first and second clamp members rotate about the pivot axis and the clamp is opened by a predetermined distance.

31. A clamp as claimed in claim 30, wherein the angle $\theta_1$ is approximately 45 degrees.

32. A clamp as claimed in claim 31, wherein
the first clamp member tissue engagement portion includes a first energy transmission element and a portion of the first energy transmission element defines the first clamp member tissue engagement surface; and
the second clamp member tissue engagement portion includes a second energy transmission element and a portion of the second energy transmission element defines the second clamp member tissue engagement surface.

33. A clamp as claimed in claim 31, wherein the first and second clamp member tissue engagement surfaces are parallel to one another and remain parallel to one another as the second clamp member pivots.

34. A clamp as claimed in claim 30, wherein the predetermined distance is about 5 mm.

35. A clamp as claimed in claim 30, wherein the predetermined distance is about 10 mm.

36. The clamp as claimed in claim 30, wherein the elongate shaft is substantially linear.

37. The clamp as claimed in claim 30, wherein a position of the first clamp member is fixed relative to the elongate shaft.

38. The clamp as claimed in claim 30, wherein the angle $\theta_2$ is approximately 45 degrees.

39. The clamp as claimed in claim 30, wherein the first and second clamp members are parallel to each other and aligned with each other when the first and second clamp members are opened by a predetermined distance.

40. The clamp as claimed in claim 30, wherein the redirect portion forms an outer surface of the clamp.

41. The clamp as claimed in claim 30, wherein the shaft forms an outer surface of the clamp.

42. The clamp as claimed in claim 30, wherein the angled portions of the respective first and second clamp members extend beyond a first side of the shaft, and the tissue engagement portions of the respective first and second members extend beyond a second, opposite side of the shaft when placed in both open and closed positions.

43. The clamp as recited in claim 30, wherein the pivot axis does not extend through the shaft.

* * * * *